United States Patent
Yamaguchi et al.

(10) Patent No.: US 7,034,694 B2
(45) Date of Patent: Apr. 25, 2006

(54) BODY MOTION DETECTOR

(75) Inventors: Kenji Yamaguchi, Chino (JP); Norimitsu Baba, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 55 days.

(21) Appl. No.: 10/669,878

(22) Filed: Sep. 25, 2003

(65) Prior Publication Data

US 2004/0116837 A1 Jun. 17, 2004

(30) Foreign Application Priority Data

Oct. 2, 2002 (JP) .............................. 2002-290007

(51) Int. Cl.
*G08B 23/00* (2006.01)
(52) U.S. Cl. ................ 340/573.1; 340/669; 340/426.1; 340/825.36; 340/554; 340/686.1; 340/573.1; 600/500; 600/510; 600/552; 600/553
(58) Field of Classification Search ............. 340/573.1, 340/669, 426.1, 825.36, 554, 686.1, 573.7; 342/357.06, 357, 352; 600/550, 552, 553, 600/500
See application file for complete search history.

(56) References Cited

U.S. PATENT DOCUMENTS

| | | | | |
|---|---|---|---|---|
| 5,430,435 A | * | 7/1995 | Hoch et al. | 340/573.7 |
| 5,694,340 A | * | 12/1997 | Kim | 702/141 |
| 6,006,129 A | * | 12/1999 | Watson | 600/546 |
| 6,204,807 B1 | * | 3/2001 | Odagiri et al. | 342/357.06 |
| 6,251,048 B1 | * | 6/2001 | Kaufman | 482/8 |

FOREIGN PATENT DOCUMENTS

JP  A 2-7943  1/1990

* cited by examiner

*Primary Examiner*—Tai T. Nguyen
(74) *Attorney, Agent, or Firm*—Oliff & Berridge, PLC

(57) ABSTRACT

The invention provides a body motion detector that allows a user to check whether he/she makes motion with appropriate motion intensity for every motion thereby to obtain an excellent exercise effect while exercising such as walking and running. While a user makes motion, a CPU determines whether the user makes appropriate motion by the amplitude, the period, and the detection frequency of an acceleration signal inputted from an acceleration sensor unit, and when it is determined that the user makes appropriate motion, operates an alarm generator thereby to notify the user that he/she makes motion with appropriate motion intensity.

13 Claims, 12 Drawing Sheets

| WALKING SPEED (m/min) | METS |
|---|---|
| 20～39 | 0～0.9 |
| 40～59 | 1.0～1.9 |
| 60～79 | 2.0～2.9 |
| 80～99 | 3.0～3.9 |
| 100～119 | 4.0～4.9 |
| 120～139 | 5.0～5.9 |

BODY MOTION DETECTOR

BACKGROUND OF THE INVENTION

1. Field of Invention

The present invention relates to a body motion detector to determine and notify appropriate motion from information on the body motion of a user while making repetitive motion.

2. Description of Related Art

Related art pitch systems to notify a predetermined period of pitch sound to a user can be used to let the user make motion at a predetermined number of pitches (for example, the number of walking pitches is 120 steps/minute.) while making repetitive motion, such as walking and running. The related art pitch systems are designed to obtain the number of walking pitches from walking time and the consumed calories, which are aimed by the user, and for a user to take a walk in accordance with the pitch sound of the number of walking pitches, thereby to obtain an excellent exercise effect, as disclosed in Japanese Unexamined Patent Application Publication No. 02-007943.

SUMMARY OF THE INVENTION

However, the related art pitch system is subject to the problem that a user cannot obtain an excellent exercise effect, even if the user makes repetitive motion, such as walking and running, in accordance with the sound of the pitch system when the motion is not appropriate (for example, the intensity of motion is weak because the shaking of arms is small and the stride step is short).

Therefore, the present invention provides a body motion detector capable of notifying whether the user makes appropriate motion (i.e., an appropriate motion intensity, appropriate motion speed, and the appropriate number of motion) for every motion while making repetitive motion, such as walking and running.

Further, the present invention provides a body motion detector that allows a user to maintain the appropriate motion intensity, the appropriate motion speed, and the appropriate number of motion by continuously notifying the user whether the motion is appropriate, and thereby to obtain an excellent exercise effect.

In order to address or achieve the above, there is provided a body motion detector, including: a body motion detecting device to detect body motion accompanying repetitive motion of a user; a determining device to determine whether the detection result of the body motion detecting device is within a predetermined reference range; and a notifying device to generate a notifying signal whenever the determination result by the determining device is within the predetermined reference range.

According to the above configuration, because a user can check whether he/she makes appropriate motion, that is, makes motion within a predetermined reference range by an notifying signal for every motion while making repetitive motion such as walking and running, it is possible for the user to make repetitive motion to obtain an excellent exercise effect while maintaining appropriate motion when the user exercises so as to obtain a determination result which is continuously positive.

The detection result is the motion intensity of the repetitive motion. According to the above configuration, because it is determined whether body motion accompanying the repetitive motion of the user has an appropriate motion intensity for every motion and a notifying signal is generated when the determination result is positive, the user can make repetitive motion capable of obtaining an excellent exercise effect while maintaining the appropriate motion intensity when the user exercises so as to obtain the determination result which is continuously positive.

Further, the detection result is the motion intensity and the motion period of the repetitive motion.

According to the above configuration, it is determined whether the body motion accompanying the repetitive motion of the user has appropriate motion period, that is, appropriate motion speed as well as the appropriate motion intensity for every motion and a notifying signal is generated when both of the motion period and the motion intensity are appropriate. Therefore, when the user exercises so as to obtain the determination result which is continuously positive, the user can make repetitive motion capable of obtaining an excellent exercise effect while maintaining the appropriate motion intensity and speed.

Furthermore, the predetermined reference range is either above a lower limit reference value set by a user or between the lower limit reference value and an upper limit reference value, which are set by the user.

According to the above configuration, it is possible to set a reference range suitable for the exercise ability or the taste of the user. Further, it is possible to prevent the user from making motion with excessively light exercise load when the user exercises so as to obtain the determination result which is continuously positive by setting the reference range above the lower limit reference value. Moreover, it is possible to prevent the user from making motion with excessively strong exercise load as well as the motion with excessively weak exercise load when the user exercises so as to obtain the determination result which is continuously positive by setting the reference range of the motion intensity between the set lower limit reference value and uppermost reference value.

Furthermore, the reference range for the motion period is calculated from motion time and an accumulated motion frequency, which are set as targets by the user.

According to the above configuration, because a lower limit motion period required to achieve the accumulated motion frequency within the motion time is calculated by setting the motion time and the accumulated motion frequency aimed by the user, it is easier for the user to set the boundary value of the reference range of the motion period.

Furthermore, the reference range for the motion period is calculated from motion time and motion calories consumed, which are set as targets by the user.

According to the above configuration, because the lower limit motion period required to consume the motion calories consumed within the motion time is calculated by setting the motion time and the motion calories consumed, which are aimed by the user, it is easier for the user to set the boundary value of the reference range of the motion period.

Furthermore, the detection result is either the motion intensity and accumulated motion frequency of the repetitive motion or the motion intensity, motion period, and accumulated motion frequency of the repetitive motion.

Furthermore, the predetermined reference range for the motion intensity and the motion period is either above the lower limit reference value set by the user or between the lower limit reference value and the upper limit reference value, which are set by the user, and where the predetermined reference range for the accumulated motion frequency is below an accumulated target frequency set by the user.

According to the above configuration, as a result of accumulating the frequency of the motion capable of providing the user with the appropriate motion intensity or the appropriate motion intensity and the appropriate motion period, when the accumulated motion frequency is below the accumulated target frequency, a notifying signal is generated. When the accumulated motion frequency is more than the accumulated target frequency, a notifying signal is not generated. Therefore, the notifying signal can be used as a signal to stop the repetitive motion.

Furthermore, when the accumulated motion frequency reaches the accumulated target frequency, the notifying device generates a notifying signal different from the notifying signal and resets the accumulated motion frequency to 0.

According to the above configuration, as a result of accumulating the frequency of the motion capable of providing the user with the appropriate motion intensity or the appropriate motion intensity and the appropriate motion period, when the frequency reaches the accumulated target frequency (hereinafter "reference motion frequency"), an a notifying signal different from the notifying signal by that time is generated. Therefore, it is possible to use the notifying signal as a signal to stop every set of motion in repetitive motion (for example, motion to strengthen muscle strength such as an abdominal muscle exercise, a spine exercise, and a squat) using several times of motion as a set.

Furthermore, the body motion detecting device includes at least one of an acceleration sensor, a pressure sensor, and a speed sensor.

Furthermore, there is provided a body motion detector, including: a body motion detecting device to detect body motion accompanying repetitive motion of a user; a determining device to determine whether the detection result of the body motion detecting device is within a predetermined reference range; a notifying device to generate a notifying signal whenever the determination result by the determining device is within the predetermined reference range; a biological reaction detecting device to detect the biological reaction of the user; and a calculating device to calculate the reference range from the detection result of the biological reaction detecting device.

According to the above configuration, it is possible to change the reference range in association with measured biological reaction information, the reference range being a reference to determine whether every motion that the user makes is appropriate. For example, in a case wherein the biological information is the pulse rate, it is possible to reset the reference range of the motion intensity as a value with weak motion intensity when the pulse rate is excessively large and as a value with strong motion intensity when the pulse rate is excessively small. As a result, it is possible to notify the user of motion suitable for the physical ability of the user.

Furthermore, the biological reaction detecting device includes a pulse wave detecting device to detect a pulse wave of the user; and pulse rate calculating device to calculate the pulse rate from the detection result of the body motion detecting device and the detection result of the pulse wave detecting device.

Furthermore, the predetermined reference range is changed so that the pulse rate is within the range of the target pulse rate when the pulse rate is beyond the range of a target pulse rate previously set by the user even if the determination result is within the predetermined reference range.

According to the above configuration, when the user walks so as to generate a notifying signal continuously, it is possible to make repetitive motion within a range of the target pulse rate. Therefore, it is possible to use the notifying signal for heart disease rehabilitation in which the management of the pulse rate is important.

Furthermore, the pulse rate calculating device analyzes the frequencies of the detection signals of the pulse wave detecting device and the body motion detecting device using FFT (fast Fourier transform) processing.

Furthermore, the notifying signal is at least one of sound from an alarm, vibration from a vibration motor, and light from an LED (light emitting diode).

DETAILED DESCRIPTION OF PREFERRED EMBODIMENTS

Exemplary embodiments of the present invention are explained below with reference to drawings. A case where the present invention is applied to a wristwatch that is an arm-wearing type device is explained assuming that user's repetitive motion is walking.

First Exemplary Embodiment

Figure 1:
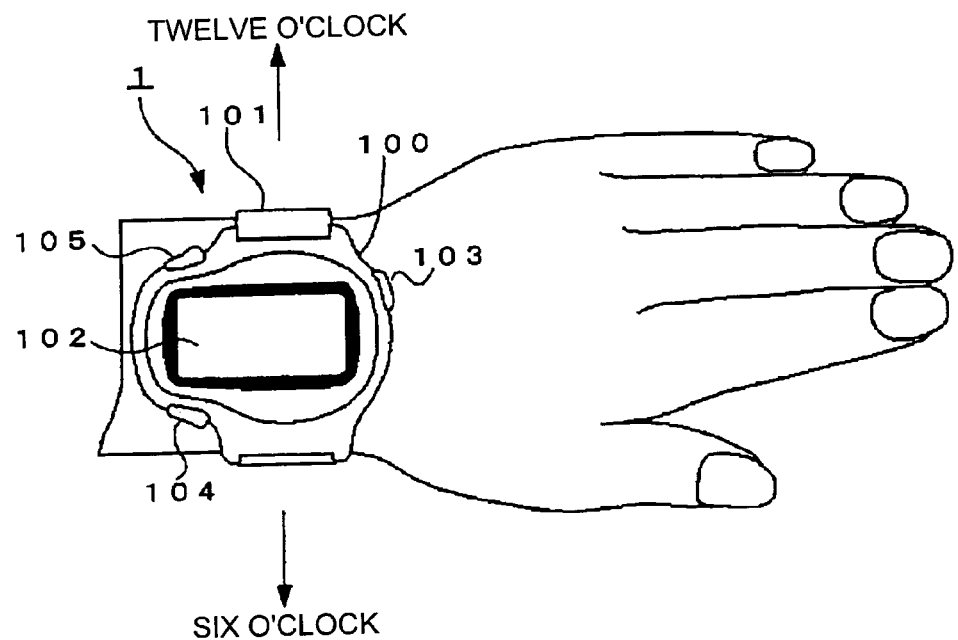
FIG. 1 is a schematic illustrating a use aspect of a body motion detector according to an exemplary embodiment of the present invention.

FIG. 1 is a schematic illustrating a use aspect of an arm-wearing type body motion detector according to an exemplary embodiment of the present invention. A body motion detector 1 includes a main body 100 having a structure of a wristwatch. The main body 100A is provided with a wristband 101 surrounding around one arm of a user from a direction of twelve o'clock and fixed to a direction of six o'clock. The main body 100 is adapted to be freely detached from and attached to the arm of the user by the wristband 101.

Figure 2:
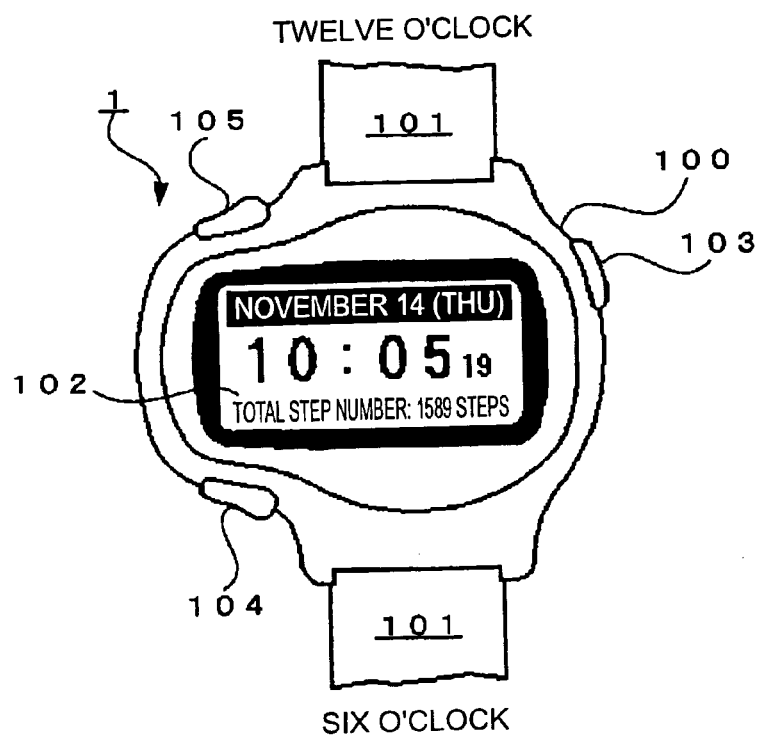
FIG. 2 is a schematic illustrating an example of the liquid crystal display of the body motion detector.

The main body 100 is provided with a liquid crystal display part 102. As illustrated in FIG. 2, the liquid crystal display part 102 is adapted to display the date, the current time, and the number of steps which is made by the user. A button switch 103 is provided in a direction of two o'clock of the outer circumference of the main body 100, and the details thereof are explained below. The pressing of the button switch 103 allows display of the liquid crystal display part 102 to be switched. A button switch 104 is provided in a direction of seven o'clock of the outer circumference of the main body 100 in addition to the button switch 103. Further, a button switch 105 is provided in the direction of eleven o'clock. The button switches 104 and 105 are used, respectively, when the user inputs various information items. Further, the button switch 105 is used to light an EL (electroluminescent) backlight provided in the liquid crystal display part 102.

Figure 3:
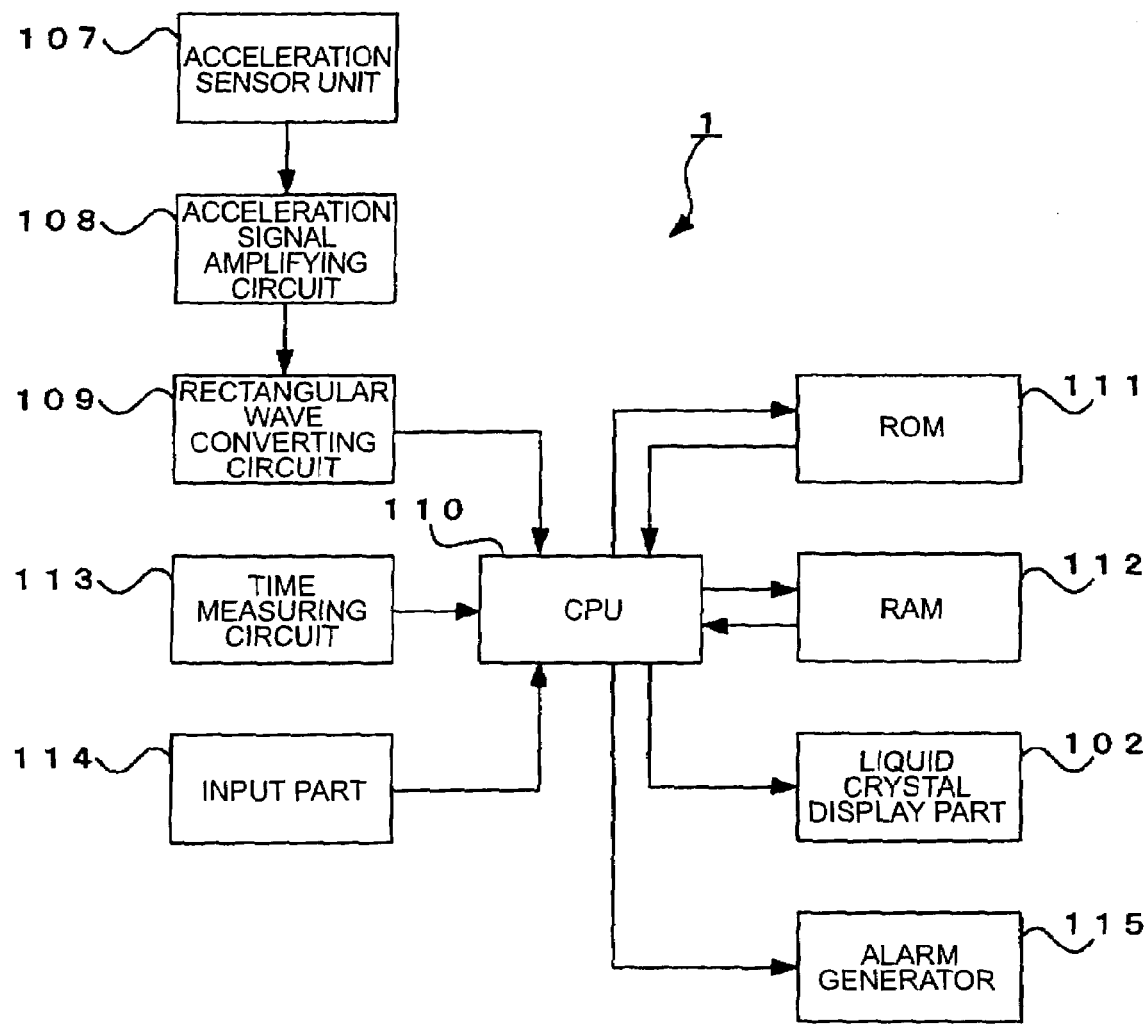
FIG. 3 is a schematic illustrating a functional configuration of the body motion detector.

FIG. 3 is a schematic illustrating the functional configuration of the main body detecting apparatus 1. In FIG. 3, a CPU 110 controls the operation of the respective parts of the body motion detector 1 as well as executes various operation processing. A ROM 111, such as an EEPROM (electrically erasable programmable ROM), is capable of rewriting data and stores a control program executed by the CPU 110 or various data. A RAM 112 is used as the work area of the CPU 110 and temporarily stores the operation result obtained by the CPU 110 or various data. The data stored by the RAM 112 is, for example, the discrete values of the date or the number of steps, and the values inputted by the user. The input values are a reference value of determining appropriate motion, such as a reference amplitude level, that is the boundary value of the reference range of the motion intensity, a reference period that is the boundary value of the reference range of the motion period, and a reference motion frequency that is the boundary value of the reference range of the motion frequency. A time measuring circuit 113 measures the time and outputs the time-measured result to the CPU 110. An input part 114 corresponds to the above-mentioned button switches 103 to 105 and outputs signals in accordance with the respective button manipulation by the user to the CPU 110. The liquid crystal display part 102 displays various information items as mentioned above and displays images on a screen according to the control of the CPU 110. An alarm generator 115 generates sound with volume in accordance with commands from CPU 110. The alarm generator 115 may generate sound, may generate a strong vibration in accordance with commands from the CPU 110, for example, by use of a vibration motor, and may emit light by a LED (light emitting diode) in accordance with commands from the CPU 110.

An acceleration sensor unit 107 is provided to detect walking that is the body motion of the user and includes an acceleration sensor to detect the acceleration of the arm-shaking motion accompanying walking. The acceleration sensor built-in the main body 100 detects the acceleration when the user shakes arms in association with walking and outputs the acceleration to an acceleration signal amplifying circuit 108 as an acceleration signal. The acceleration signal amplifying circuit 108 converts the received acceleration signal into a voltage value, amplifies the voltage value, and outputs it as a substantial sine wave 1160 illustrated in FIG. 4 to a rectangular wave converting circuit 109.

Figure 4:
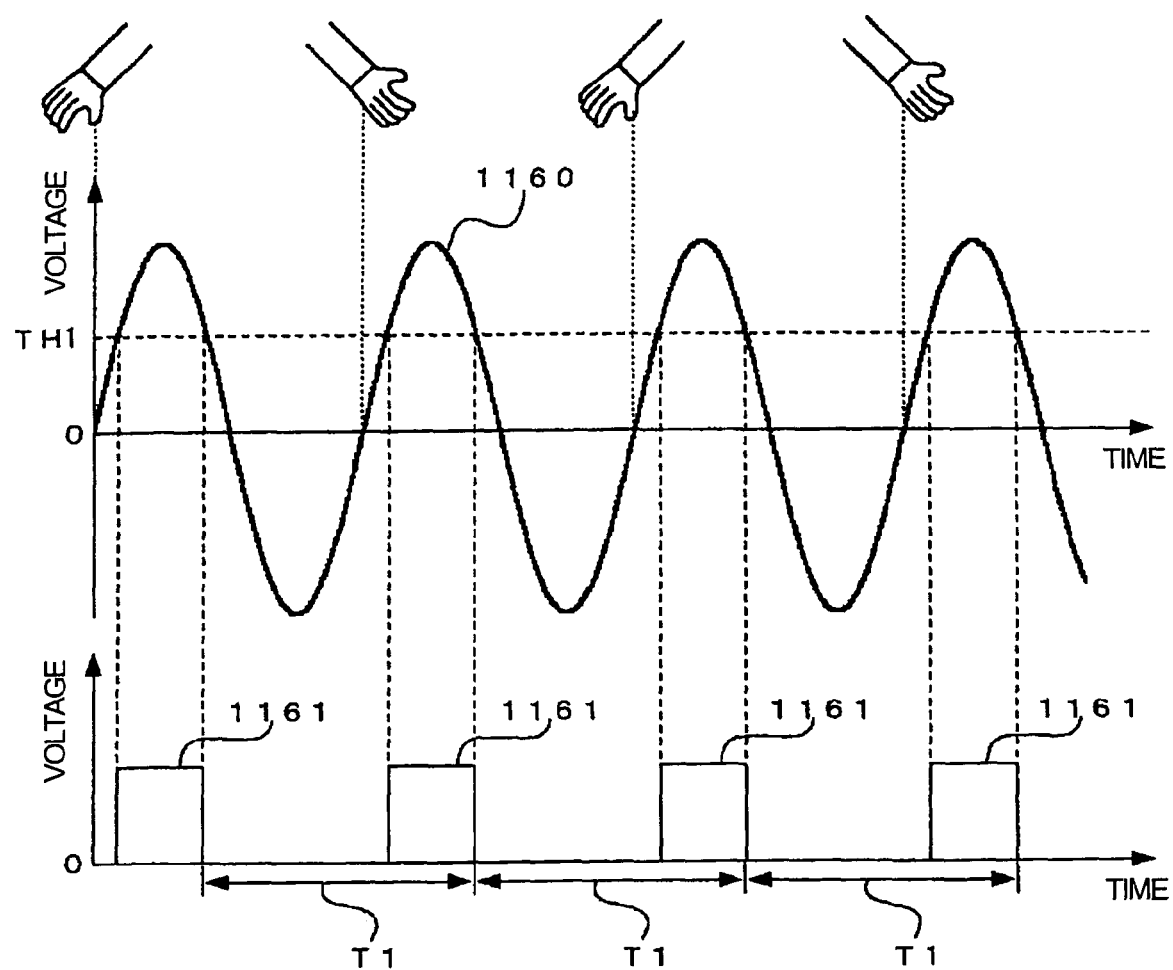
FIG. 4 is a schematic showing the operation of a rectangular wave circuit.

The rectangular wave converting circuit 109 sequentially shapes the waveform of the acceleration signal outputted from the acceleration signal amplifying circuit 108 to the substantially rectangular wave. More specifically, as illustrated in FIG. 4, the rectangular wave converting circuit 109 forms rectangular wave pulses 1161 when the amplitude value of the substantial sine wave 1160 outputted from the acceleration signal amplifying circuit 108 exceeds a predetermined threshold TH1. Because the amplitude value of the acceleration signal is interlocked with the intensity of shaking arms accompanying walking of the user. The more intensive the motion of the arms of the user is, the larger the amplitude value. The rectangular wave converting circuit 109 outputs a walking-detecting signal to the CPU 110 whenever the rectangular wave pulses 1161 are formed. The CPU 110 operates an alarm generator 115 whenever walking detecting signal is received from the rectangular wave converting circuit 109, to notify the user that he/she has taken a walk with predetermined motion intensity.

That is, the alarm generator is set to generate an alarm sound whenever the user shakes arms with motion intensity above a certain reference value. The alarm sound is not generated when the user shakes arms with the motion intensity below the reference value. Therefore, the user can sense the motion intensity that becomes the reference value by shaking arms (taking a walk) while listening to the presence of the alarm sound. Further when the user shakes arms (takes a walk) so that the alarm sound is continuously generated, the user can take a walk with an excellent exercise effect while maintaining the motion intensity that is above the reference value.

The CPU 110 counts the frequency of receiving walking detecting signal, that is, the number of steps, causes the number of steps to be stored in the RAM 112, accumulates the period (the seconds) of the rectangular wave pulses 1161 that is walking detecting signal, thereby to calculate walking time, and causes walking time to be stored in the RAM 112.

The threshold TH1, when the rectangular wave converting circuit 109 forms the rectangular wave pulses 1161, for example, can be set to an arbitrary value by the reference amplitude level that is the boundary value of the reference range of the intensity inputted from the input part 114. The reference amplitude level is obtained by statistically calculating the acceleration of shaking arms, which accompanies walking, from the result measured with a plurality of Japanese and corresponds to the threshold TH1. More specifically, the average value A and the standard deviation $\sigma$ of the amplitude of the acceleration signal are obtained from the measurement result. As illustrated in the Expression 1, the value obtained by adding the double of the standard deviation $\sigma$ to the average value A is the reference amplitude level of "Strong". As illustrated in the Expression 2, the value obtained by subtracting the standard deviation $\sigma$ from the average value A is the reference amplitude level of "Normal". As illustrated in the Expression 3, the value obtained by subtracting the double of the standard deviation $\sigma$ from the average value A is the reference amplitude level of "Weak".

Reference Amplitude Level of "Strong"=Average Value $A$+(2×Standard Deviation $\sigma$) (Expression 1)

Reference Amplitude Level of "Normal"=Average Value $A$−Standard Deviation $\sigma$ (Expression 2)

Reference Amplitude Level of "Weak"=Average Value $A$−(2×Standard deviation $\sigma$) (Expression 3)

The user can input a selection item among the selection items, such as "Strong", "Normal", and "Weak" suitable for the his/her taste. The input of the reference amplitude level is described below in more detail.

Further, the reference amplitude level can be set as an arbitrary plurality of amplitude levels such as levels 1, 2, 3, . . . , and 10.

As mentioned above, the CPU 110 operates the alarm generator 115 by determining whether the amplitude value of the substantial sine wave 1160 exceeds the threshold TH1, that is, whether the user exercises with an appropriate motion intensity. In addition, it is possible to determine whether the user exercises at appropriate motion period (i.e., at appropriate motion speed) and thereby to operate the alarm generator 115 when the both of the determinations results are positive.

More specifically, as illustrated in FIG. 4, when a period T1 from the falling of a pulse to the falling of a next pulse is within a predetermined time range (hereinafter, a reference period) in the rectangular wave pulses 1161 outputted from the rectangular wave converting circuit 109, it is determined that the rectangular wave pulses 1161 are walking detecting signals. As a result, it is notified that the user takes a walk with predetermined walking intensity and at predetermined walking speed by operating the alarm generator 115. Therefore, when the user exercises so that the alarm sound is continuously generated, the user can take a walk, which enables to obtain an excellent exercise effect while maintaining the appropriate walking intensity and speed.

The period T1 corresponds to the time taken for one time of arm shaking, which accompanies walking of the user, that is, the time taken for a step. More specifically, when the period T1 is long, the number of walking pitches (steps/min) is short. When the period T1 is short, the number of walking pitches is large. Therefore, it is possible to prevent the user from taking an excessively fast walk in which the period T1 is shorter than the reference period and from taking an excessively slow walk in which the period T1 exceeds the reference period, thereby to notify the accurate walking operation to the user.

Further, the reference period when the CPU 110 determines walking detecting signal can be set to an arbitrary value by the number of walking pitches (walks/min) inputted from the input part 114. The CPU 110, as illustrated in the Expression 4, calculates the reference period from the input number of walking pitches and causes the reference period to be stored in the RAM 112.

Reference Period (sec)=60/number of walking pitches (walks/min)  (Expression 4)

Furthermore, the CPU 110 counts the frequency of operating the alarm generator 115, that is, the frequency of performing the appropriate walks. When the frequency becomes the predetermined frequency (the reference motion frequency), a process of operating the alarm generator 115 with a tone different from that of the notifying sound of detecting walking by that time is repeated, thereby to initialize the frequency of operating the alarm generator 115 to 0. Therefore, the user can use the notifying signal as a signal to stop every set of motion in repetitive motion (for example, motion to strengthen muscle strength, such as the forces of an abdominal muscle exercise, a spine exercise, and a squat) having several times of motion as a set in addition to a signal to confirm the motion intensity and the motion speed.

Figure 12:
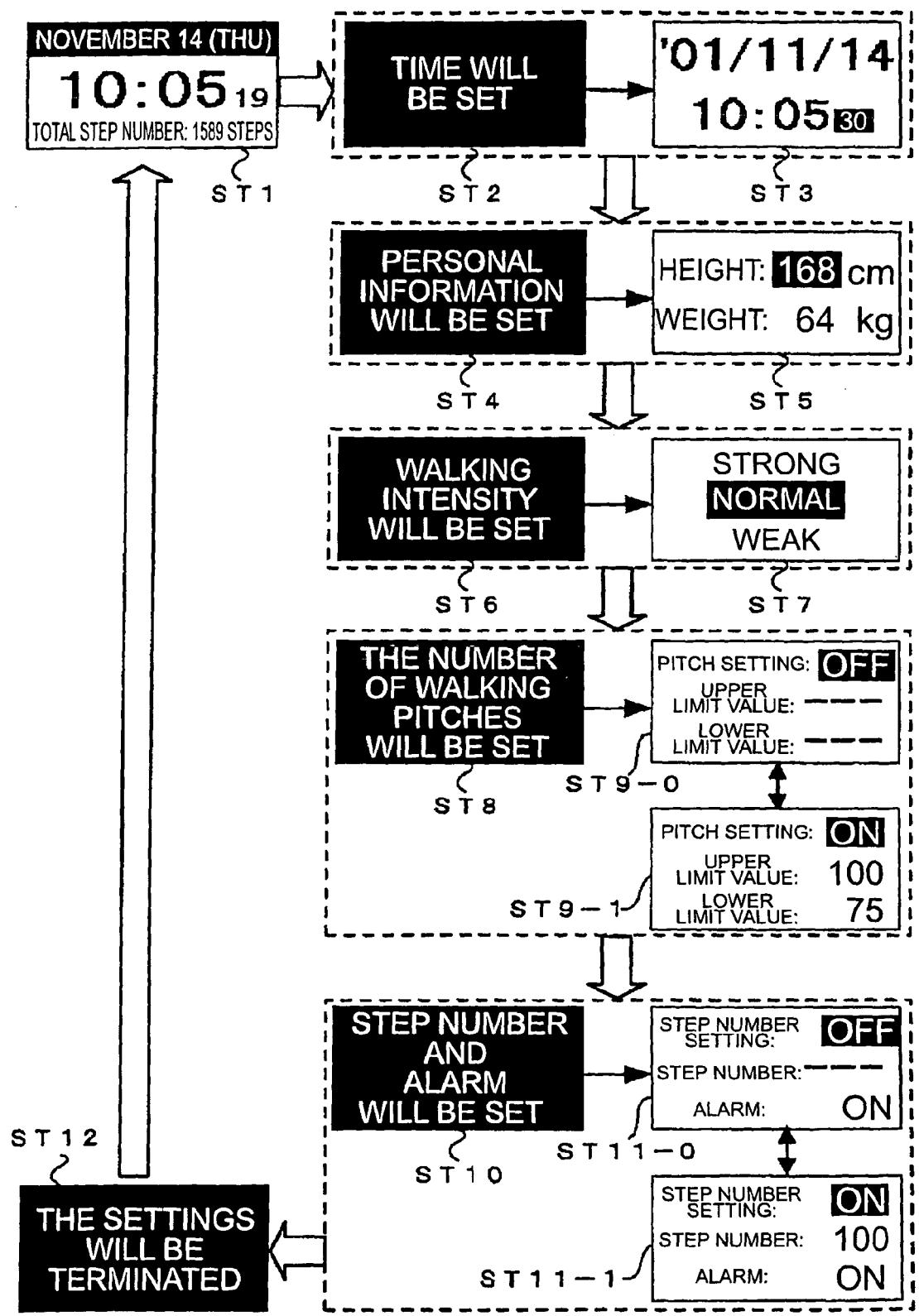
FIG. 12 is a schematic illustrating transition of a display screen.

The specific operation when the body motion detector 1 is used is described in detail below. The user first sets the date and the current time when the body motion detector 1 is first used. Then, the user sets walking intensity (i.e., the reference amplitude level), the number of walking pitches (i.e., the reference period), and the number of steps (i.e., the reference motion frequency) that are the determination conditions when the CPU 110 operates the alarm generator 115. Specifically, when the user continuously presses the button switch 103 for a predetermined time (for example, for three seconds) in a state where a standard screen ST1 to display the date, the time, and the total number of steps of a day is displayed on the liquid crystal display part 102 as illustrated in FIG. 12, the CPU 110 senses related manipulation and causes a time setting and notifying screen ST2 to notify setting the time to the user to be displayed on the liquid crystal display part 102. Subsequently, when the user presses the button switch 103, the CPU 110 causes a time setting screen ST3 to be displayed on the liquid crystal display part 102. The reversed display with strong contrast is made on the time setting and notifying screen ST2 so as to allow the user to easily know motion to be made next. The reversed display is made on the following notifying screens due to the same reason.

Meanwhile, the reversed display of numbers to be set is made on the time setting screen ST3 (In the illustrated example, the seconds are to be set.). When the time setting screen ST3 is initially displayed, it is set so that the year of the date is reversed as an initial object to be set. The user sets the date and the time in the order. When the user presses the button switches 104 and 105, the numbers of the object to be set are changed. Specifically, the CPU 110 reduces the number of the object to be set whenever the button switch 104 is pressed, whereas it increases the number of the object to be set whenever the button switch 105 is pressed. When the user presses the button switch 103, the CPU 110 reverses the display of the object to be set. Therefore, the year of the date to the second of the current time are sequentially set by the user.

When the user presses the button switch 103 in a state where the display of the object to be finally set (in the illustrated example, the second is to be finally set) in the time setting screen ST3 is being reversed, the CPU 110 causes the date and the current time, which have been modified, to be stored in the RAM 112. Then, the CPU 110 causes a personal information setting and notifying screen ST4 to be displayed on the liquid crystal display part 102 so as to urge the user to input personal information. When the user presses the button switch 103, the CPU 110 causes a personal information setting screen ST5 to be displayed on the liquid crystal display part 102.

In the personal information setting screen ST5, the height and the weight of a user are set as the personal information of the user. The respective objects to be set are set similarly to the order described with respect to the time setting screen ST3. When the user presses the button switch 103 in a state where the display of the final object to be set (in the illustrated example, the height is to be set) is reversed on the personal information setting screen ST5, the CPU 110 causes the set personal information (the height and the weight) to be stored in the RAM 112 and causes a walking intensity setting and notifying screen ST6 to be displayed on the liquid crystal display part 102 so as to urge the user to input walking intensity (i.e., the reference amplitude level). At this time, when the user presses the button switch 103, the CPU 110 causes walking intensity setting screen ST7 to be displayed on the liquid crystal display part 102.

In walking intensity setting screen ST7, as mentioned above, walking intensity (i.e., the reference amplitude level) is set, which is a determination condition when it is determined whether the CPU 110 operates the alarm generator 115. One item is selected among "Strong", "Normal", and "Weak" as walking intensity as mentioned above. The display of the selected item is reversed (In the illustrated example, "Normal" is selected.). When walking intensity setting screen ST7 is initially displayed, the display of "Normal" of walking intensity is reversed as the selected item. Walking intensity is selected by the user's pressing of the button switches 104 and 105.

Then, when the user presses the button switch 103, the CPU 110 causes the selected walking intensity to be stored in the RAM 112. Next, the CPU 110 causes a walking pitch number setting and notifying screen ST8 to be displayed on the liquid crystal display part 102 so as to urge the user to input the number of walking pitches (i.e., the reference period). At this time, when the user presses the button switch 103, the CPU 110 causes a walking pitch number setting screen ST9-0 to be displayed on the liquid crystal display part 102.

In walking pitch number setting screen ST9-0, as mentioned above, the number of walking pitches (i.e., the reference period) is set, which is a determination condition when it is determined whether the CPU 110 operates the alarm generator 115. In setting the number of walking pitches, first, it is selected whether the number of walking pitches is used as a condition of determining whether to generate the alarm sound by setting ON/OFF. The display of ON/OFF is reversed, which is an object to be set. Therefore, whenever the user presses the button switch 105, the CPU 110 alternates the display of ON/OFF.

When the user presses the button switch 103 while the display of ON as a selected item is reversed, the CPU 110 causes a walking pitch number setting screen ST9-1 to be displayed on the liquid crystal display part 102. In walking pitch number setting screen ST9-1, the lower limit value and the upper limit value of the number of walking pitches are set. When walking pitch number setting screen ST9-1 is initially displayed, the display of the lower limit value of the number of walking pitches as an object to be set is reversed. The numbers of the object to be set are changed similarly to the order described with respect to the time setting screen ST3. Then, when the user presses the button switch 103 in a state where the display of the upper limit value of the number of walking pitches as an object to be set is reversed, the CPU 110 causes the fact that the setting of the number of walking pitches is ON, the lower limit value and the upper limit value of the number of walking pitches to be stored in the RAM 112.

Meanwhile, when the user presses the button switch 103 while the display of OFF as a selected item is reversed, the CPU 110 causes the fact that the setting of the number of walking pitches is OFF to be stored in the RAM 112.

As described above, the CPU 110 causes a step number setting and notifying screen ST10 to be displayed on the liquid crystal display part 102 so as to urge the user to input the number of steps (i.e., the reference motion frequency) after causing the setting of the number of walking pitches to be stored in the RAM 112. At this time, when the user presses the button switch 103, the CPU 110 causes a step number setting screen ST11-0 to be displayed on the liquid crystal display part 102.

In the step number setting screen ST1-0, as mentioned above, the number of steps (i.e., the reference motion frequency) is set, which is a determination condition when it is determined whether the CPU 110 operates the alarm generator 115 with a tone different from that of the notifying sound of detecting walks by that time, and ON/OFF of the alarm sound is also set. The number of steps is set similarly to the order described with respect to walking pitch number setting screens ST9-0 and ST9-1.

Then, when the user presses the button switch 103 in a state where the display of the number of steps that is an object to be set is reversed, the CPU 110 causes the setting of the number of steps to be stored in the RAM 112 and causes the display of ON/OFF of the alarm sound as an object to be set to be reversed.

In setting the alarm sound, whenever the user presses the button switch 105, the CPU 110 alternates the display of ON/OFF. When the alarm sound is set as OFF, the CPU 110 does not operate the alarm generator 115. Therefore, the user cannot checks whether he/she makes appropriate motion whenever the user walks. However, because the number of steps is counted, the wristwatch can be used as a general wristwatch functioning as a pedometer (a registered trademark).

Next, in setting the alarm sound, when the user presses the button switch 103, the CPU 110 causes ON/OFF of the alarm sound to be stored in the RAM 112 and a setting termination notifying screen ST12 to be displayed on the liquid crystal display part 102 so as to notify the user that the setting is completed. When the user presses the button switch 103, the CPU 110 causes a standard screen ST1 to be displayed on the liquid crystal display part 102. As a result, the setting of various information items is completed.

Meanwhile, when it notifies whether the user makes appropriate motion whenever the user takes a walk using the body motion detector 1, the user takes a walk in a state where the standard screen ST1 is displayed on the liquid crystal display part 102. In this regard, the CPU 110 determines whether to operate the alarm generator 115, from the acceleration signal of arm shaking, which accompanies walking, outputted from the rectangular wave converting circuit 109, and the values set in the previously mentioned walking intensity setting screen, walking pitch number setting screen, and the walk number setting screen and notifies the user whether he/she makes appropriate motions. Further, the CPU 110 counts the number of steps, causes the number of steps to be stored in the RAM 112, and updates display of the total number of steps per day on the standard screen ST1.

Figure 13:
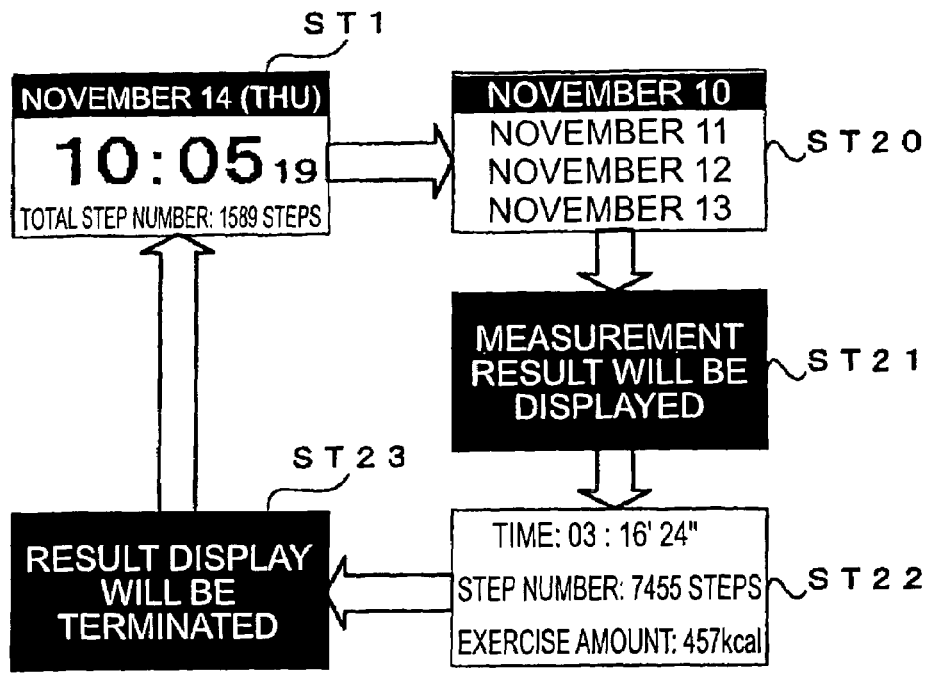
FIG. 13 is a schematic illustrating transition of the display screen.

In order to display various information items, such as the total walking time, the total number of steps, and the total amount of motion per day, which are stored in the RAM 112, on the liquid crystal display part 102, the user presses the button switch 104 when the standard screen ST1 is displayed. When the CPU 110 senses such manipulation, as illustrated in FIG. 13, the CPU 110 causes a date selection screen ST20 for urging the user to select the date to be displayed for displaying a result of measurement. The display of the selected date is reversed on the date selection screen ST20. Therefore, so as to select the date, the user presses the button switch 105.

Meanwhile, when the user selects the date by pressing the button switch 105 and presses the button switch 104, the CPU 110 causes a result display-notifying screen ST21 to notify the purport of displaying the measurement result to the user to be displayed on the liquid crystal display part 102. At this time, when the user presses the button switch 104, the CPU 110 causes a daily exercise amount-displaying screen ST22 to be displayed on the liquid crystal display part 102.

The amount of motion per day of the previously selected date, that is, the total walking time, the total number of steps, and the total amount of motion per day are displayed on the daily exercise amount-displaying screen ST22. When the user presses the button switch 104 in a state where the daily exercise amount displaying screen ST22 is displayed on the liquid crystal display part 102, the CPU 110 causes a result display termination notifying screen ST23 to be displayed on the liquid crystal display part 102. At this time, when the user presses the button switch 104, the CPU 110 causes the standard screen ST1 to be displayed on the liquid crystal display part 102 and stops displaying various measurement results.

Further, the above mentioned exercise amount is obtained from the Expression 5.

Exercise amount (kcal)≈METS×Weight (kg)×Motion Time (hour)     (Expression 5)

METS (Metabolic Equivalents) is an index showing how many times the exercise amount is larger than the energy consumption amount in stability. The METS was published by the America College of Sport Medicine (ACSM) and is generalized as a unit of measuring the intensity of exercise. Specifically, the METS shows the ratio of the oxygen consumption amount in motion to the oxygen consumption amount in stability when the oxygen consumption amount in stability is 3.5 ml/kg/min. The relationship of the Expression 6 is established between the METS and the energy consumption amount.

1METS≈1 kcal/kg/hour     (Expression 6)

Figures 8, 9:
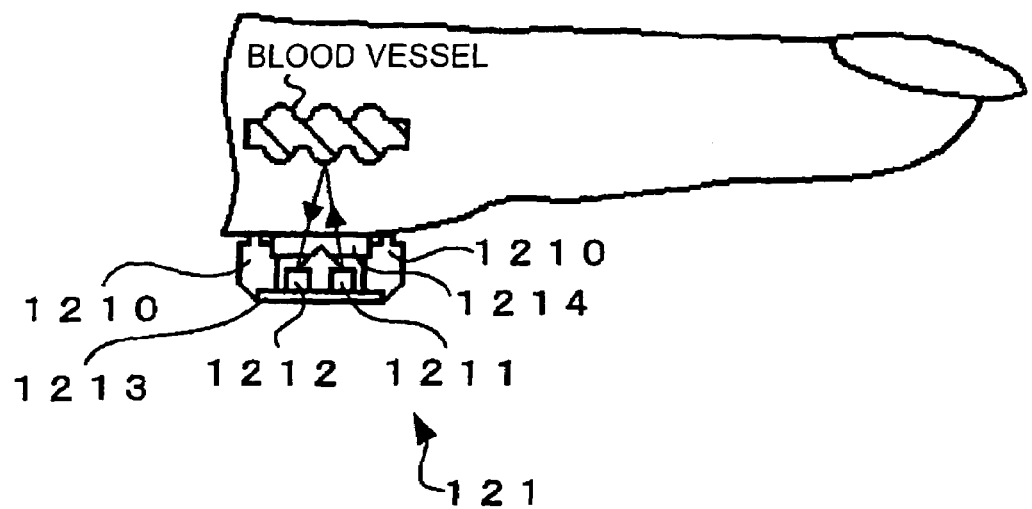
FIG. 8 is a schematic illustrating a configuration of a pulse wave sensor unit.
FIG. 9 is a schematic illustrating a correspondence relationship between the METS and walking speed.

The METS is obtained from walking speed (m/min). The value, into which the correspondence relationship between the METS published by the ACSM and walking speed is converted so as to simply and easily calculate the correspondence relationship, is illustrated in FIG. 9. Therefore, the METS in motion is specified and the exercise amount is obtained by obtaining walking speed in the motion. Walking speed is obtained from the Expression 7.

Walking speed (m/min)=Step (m)×Number of Steps/ Walking time (min)     (Expression 7)

Step (cm) Height (cm)–100 (cm)     (Expression 8)

Walking speed of the Expression 8 is walking distance per unit walking time. Walking distance is calculated by multiplying the step by the number of steps. Further, the step is the distance from a heel to the other heel of both feet when the user takes a walk. The method of simply calculating the step, which is shown in the Expression 8, is applied to a case where an adult commonly takes a walk. In the case of calculating the motion consumption amount with high precision, it is preferable that the user input a correct step.

Therefore, the step is obtained from the height set by the user according to the Expression 8. Further, walking speed is obtained from this step and the measured number of steps and motion time according to the Expression 7. The METS in motion is specified from the correspondence relationship between the METS and walking speed illustrated in FIG. 9. The exercise amount is obtained by the Expression 5. The CPU 110 calculates the exercise amount as mentioned above and causes the measurement result including the exercise amount to be stored in the RAM 112.

(Second Exemplary Embodiment)

Next, an exemplary embodiment of an arm-wearing type body motion detector obtained by adding a biological information measuring function to the body motion detector 1 according to the above-mentioned exemplary embodiment is explained in more detail below. In particular, the biological information measuring function, which is newly added to the body motion detector 1, and the form thereof is mainly described below.

Figure 6:
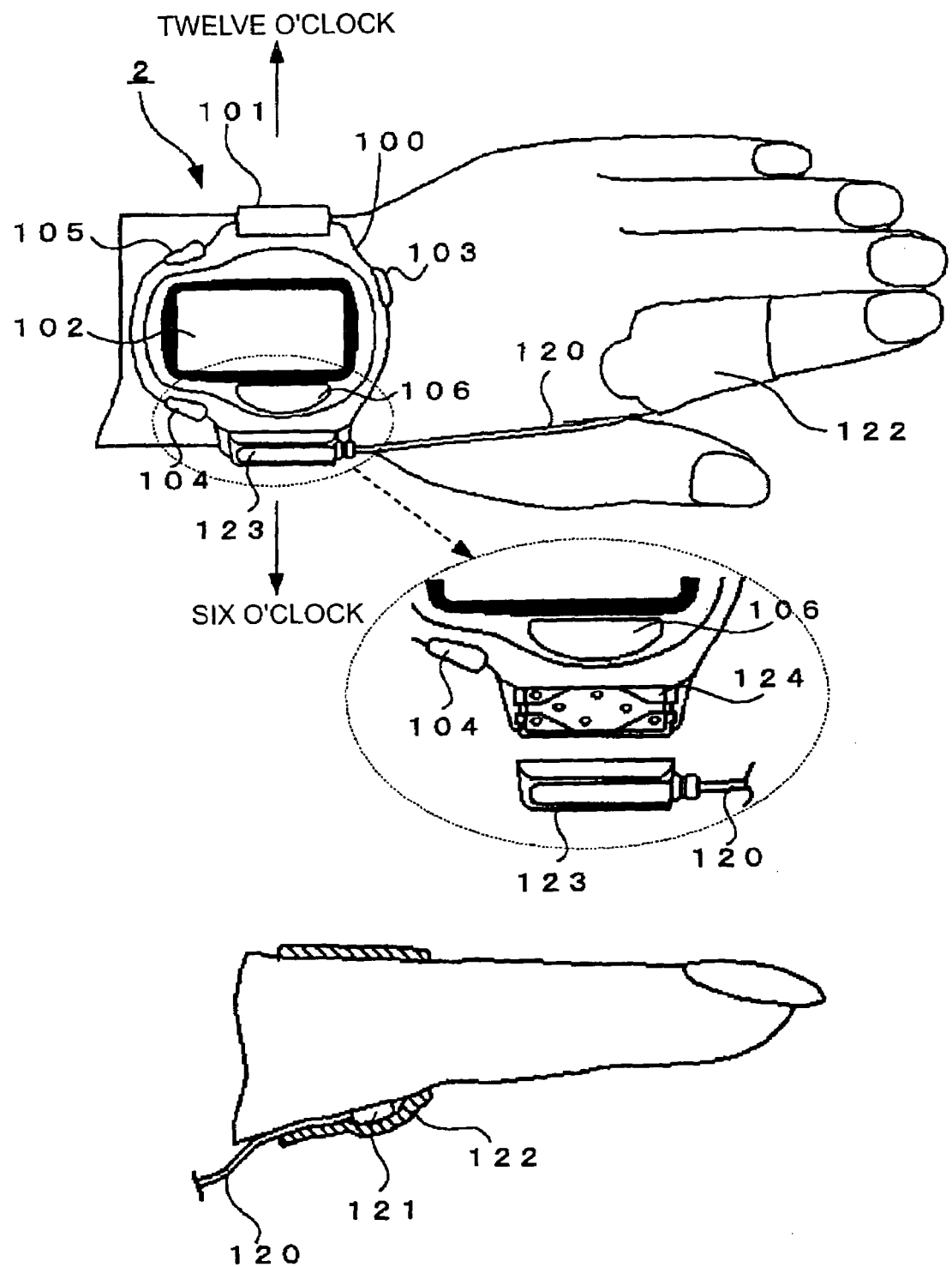
FIG. 6 is a schematic illustrating a use aspect of a device obtained by an adding biological information detecting device to the body motion detector.

FIG. 6 is a schematic illustrating a use aspect of the arm-wearing-type body motion detector obtained by adding the biological information measuring function to the body motion detector 1 illustrated in FIG. 1. The body motion detector 2 includes all of the functions of the above-mentioned body motion detector 1.

As illustrated in FIG. 6, the surface of the liquid crystal display part 102 of the main body 100 is provided with a start/stop button 106. The start/stop button 106 is used so that the user instructs the corresponding body motion detector 1 to start or stop measuring the number of steps that is the body motion information and the pulse rate that is biological information while exercising. Further, a connector 124 is provided on the outer circumference of the main body 100 in a direction of six o'clock. A connector piece 123 is mounted in the connector 124 to be detachably attached thereto. One end of a cable 120 is connected to the connector piece 123, while a pulse wave sensor unit 121 to measure the pulse rate of the user is connected to the other end of the cable 120. The pulse wave sensor unit 121 is fixed under a finger of the user by a sensor-fixing band 122. According to the above configuration, because the connector piece 123 is detachably attached to the connector 124, the user can use the present device as the body motion detector 1 described in the exemplary embodiment 1 or a wristwatch by removing the connector piece 123 from the connector 124.

Furthermore, a certain connector cover (not shown) is included in the body motion detector 2 in a state where the cable 120 and the pulse wave sensor unit 121 are removed from the connector 124 so as to protect the connector 124. A part in which an electrode is removed from parts, which are configured similarly to the connector piece 123, is used as the connector cover. According to the connector thus constructed, because the connector 124 is arranged in front of the user in viewing from the user, the user can easily manipulate the connector 124. Further, because the connector 124 does not protrude from the main body 100 toward the direction of three o'clock of the wristwatch, the back of the hand of the user does not contact the connector 124, thereby does not prevent the motion of the wrist of the user to be restricted.

Figure 7:
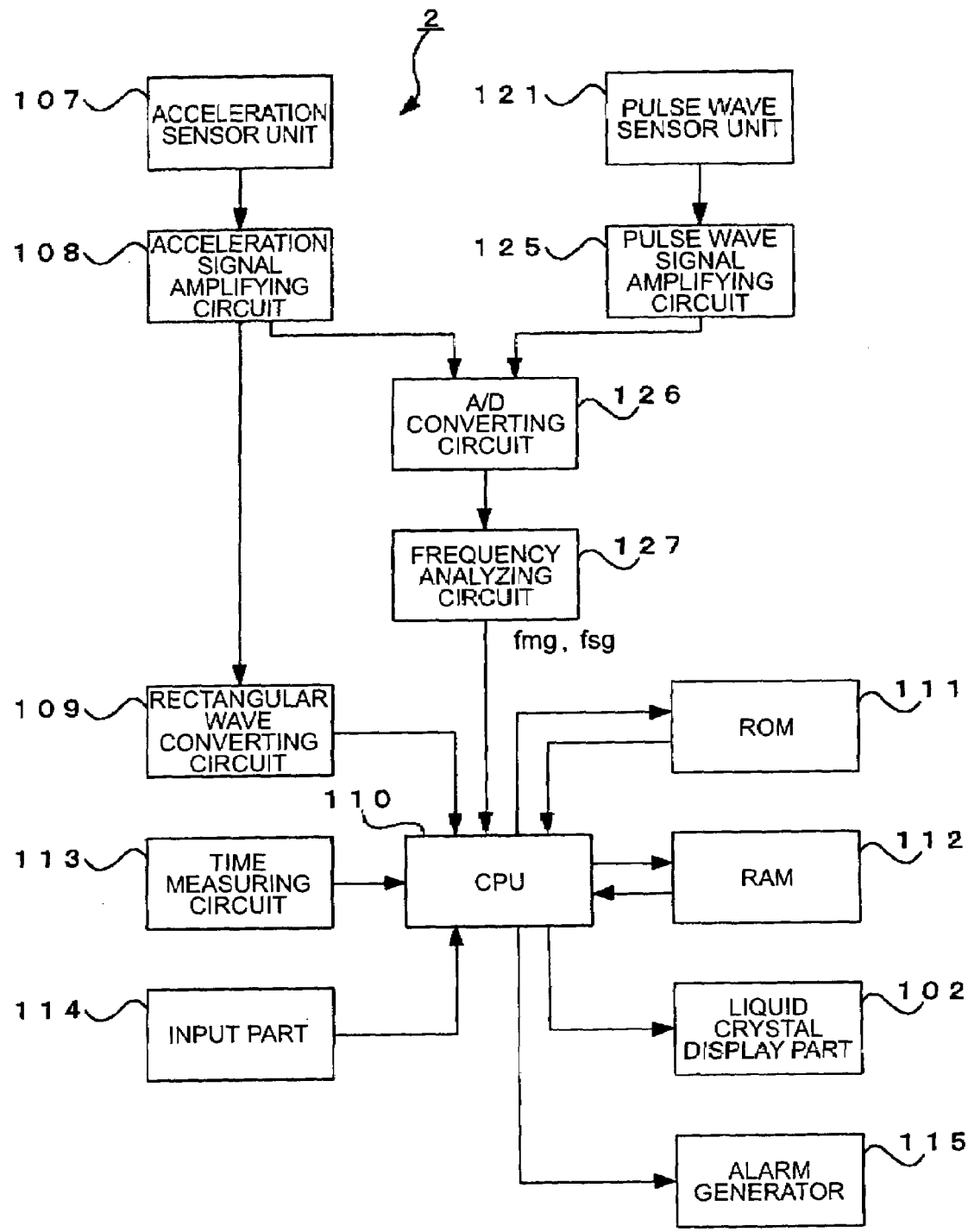
FIG. 7 is a schematic illustrating a functional configuration of the device obtained by adding the biological information detecting device to the body motion detector.

FIG. 7 is a schematic illustrating the functional configuration of the body motion detector 2. The body motion detector 2 includes a pulse wave sensor unit 121, a pulse wave signal amplifying circuit 125, an A/D converting circuit 126, and a frequency analyzing circuit 127 so as to execute a function to measure the pulse rate of the user in addition to the functional configuration of the body motion detector 1 illustrated in FIG. 2.

The pulse wave sensor unit 121, as mentioned above, detects the pulse wave that is the biological reaction of the user and outputs the pulse wave as a pulse wave signal to the pulse wave signal amplifying circuit 125. More specifically, as illustrated in FIG. 8, the pulse wave sensor unit 121 includes a sensor frame 1210 as a case main body. An LED 1211, a phototransistor 1212, and a circuit board 1213 are provided inside the sensor frame 1210. A transmitting plate 1214 formed of a glass plate is provided in a direction of the light emission from the LED 1211. The circuit board 1213 is arranged to face the transmitting plate 1214. According to the above configuration, light emitted from the LED 1211 is reflected through the blood vessel under the skin of the user and is received by the phototransistor 1212. As a result of performing photoelectric conversion in the phototransistor 1212, a pulse wave detecting signal is obtained and is outputted to the pulse wave signal amplifying circuit 125 built in the main body 100 through the cable 120 connected to the circuit board 1213. Electric power is supplied from a battery (not shown) built in the main body 100 to the pulse wave sensor unit 121 through the cable 120.

The pulse wave signal amplifying circuit 125 amplifies a pulse wave signal from the pulse wave sensor unit 121 and outputs the pulse wave signal to the A/D converting circuit 126. The A/D converting circuit 126 converts the received pulse wave signal from analog to digital and outputs the converted pulse wave signal to the frequency analyzing circuit 127 only while a control signal is inputted from the CPU 110. In more detail, the CPU 110 outputs the control signal to the A/D converting circuit 126 when the A/D converting circuit 126 is operated. That is, when the CPU 110 does not output the control signal to the A/D converting circuit 126, the pulse wave signal from the pulse wave signal amplifying circuit 125 is nullified in the A/D converting circuit 126. The frequency analyzing circuit 127 receives a pulse wave signal converted into a digital signal for a predetermined period of time and performs fast Fourier transform (FFT) processing on the digital signal, thereby to extract the frequency component of the pulse wave signal and to output the frequency component to the CPU 110 as a pulse wave spectrum signal fing.

An acceleration sensor unit 107, as mentioned above, detects walking that is the body motion of the user and outputs walking as an acceleration signal to an acceleration signal amplifying circuit 108. The acceleration signal amplifying circuit 108, as mentioned above, amplifies the received acceleration signal and outputs the acceleration signal to a rectangular wave converting circuit 109 and also to the A/D converting circuit 126. The A/D converting circuit 126, as mentioned above, converts the received acceleration signal from analog to digital and outputs the converted acceleration signal to the frequency analyzing circuit 127 only while the control signal is inputted from the CPU 110. More specifically, the A/D converting circuit 126 alternately receives the pulse wave signal from the pulse wave signal amplifying circuit 125 and the acceleration signal from the acceleration signal amplifying circuit 108 every predetermined time (i.e., time sharing) and outputs the pulse wave signal and the acceleration signal to the frequency analyzing circuit 127. The frequency analyzing circuit 127 receives the acceleration signal converted into the digital signal for a predetermined period of time and performs the FFT processing on the digital signal, thereby to calculate the frequency component of the acceleration signal and to output the frequency component to the CPU 110 as an acceleration spectrum signal fsg.

As described above, the pulse wave spectrum signal fmg and the acceleration spectrum signal fsg that are outputted from the frequency analyzing circuit 127, are alternately inputted to the CPU 110, respectively. The CPU 110 calculates the pulse wave from the pulse wave spectrum signal fmg and the acceleration spectrum signal fsg thereby to obtain the pulse rate.

Figure 10:
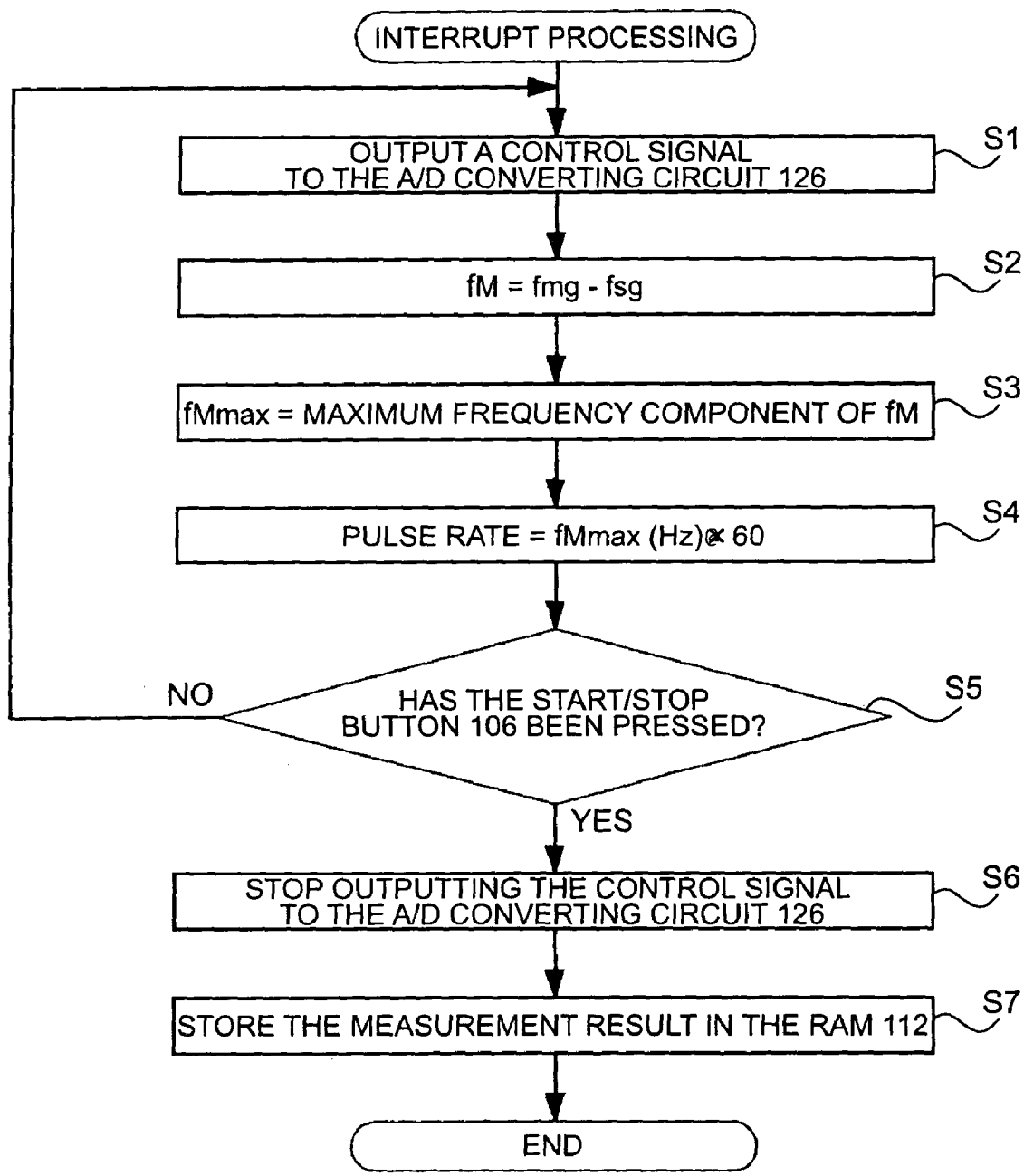
FIG. 10 is a flow chart illustrating the order of an interrupt processing performed by a CPU.

More specifically, the measurement of the pulse rate starts by the user's pressing of the start/stop button 106. An interrupt processing illustrated in FIG. 10 is executed. As illustrated in FIG. 10, the CPU 110 outputs the control signal to the A/D converting circuit 126 and operates the A/D converting circuit 126 that is not in operation state so as to obtain a signal from the frequency analyzing circuit 127 (step S1). As a result, the pulse wave signal and the acceleration signal converted into the digital signals by the A/D converting circuit 126 are outputted to the frequency analyzing circuit 127. The frequency analyzing circuit 127 receives the pulse wave signal and the acceleration signal converted into the digital signals for a predetermined period of time, performs the FFT processing on the digital signals, and outputs the pulse wave spectrum signal fing and the acceleration spectrum signal fsg to the CPU 110.

Figure 11A:
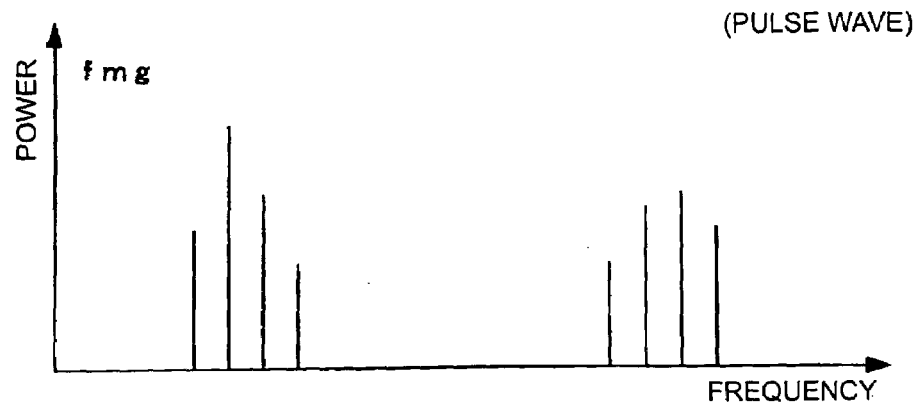
FIG. 11A is a schematic illustrating a pulse wave spectrum signal.
Figure 11B:
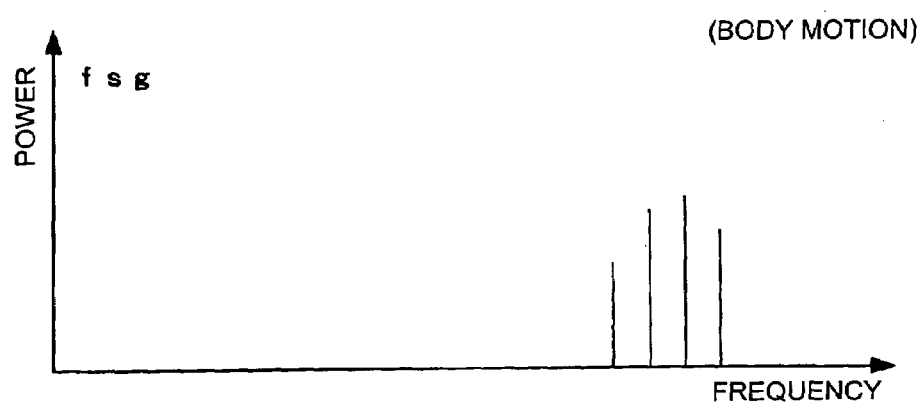
FIG. 11B is a schematic illustrating an acceleration spectrum signal.

The CPU 110 extracts the pulse wave component so as to calculate the pulse rate when the pulse wave spectrum signal fing and the acceleration spectrum signal fsg are received. That is, the CPU 110 subtracts the acceleration spectrum signal fsg from the pulse wave spectrum signal fmg and calculates a subtracted spectrum signal fM (step S2). The subtraction of the acceleration spectrum signal fsg from the pulse wave spectrum signal fing is based on the following reason. That is, as illustrated in FIG. 11A, the acceleration spectrum signal fsg as the frequency component according to the body motion (i.e., the motion of arms) is also included in the pulse wave spectrum fmg detected while exercising (see FIG. 11B). Thus, the acceleration spectrum signal fsg is subtracted from the pulse wave spectrum signal fing so as to remove this acceleration spectrum signal fsg.

Figure 11C:
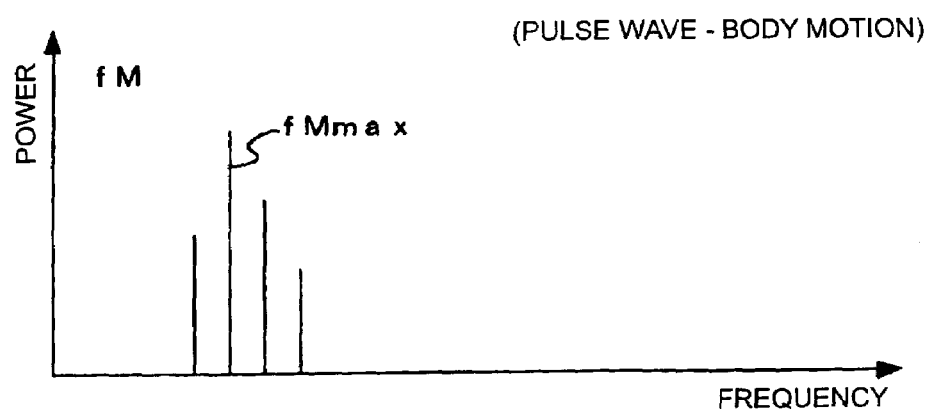
FIG. 11C is a schematic illustrating subtraction of an acceleration spectrum signal from the pulse wave spectrum signal.

Next, as illustrated in FIG. 11C, the maximum frequency fMmax that has the highest power as a frequency equivalent to the pulse wave is obtained among the frequency components included in the subtracted spectrum fM (step S3). After obtaining the pulse wave fMmax as mentioned above, the CPU 110 calculates the pulse rate (pulses/min) by substituting the maximum frequency fMmax (i.e., the pulse wave) obtained in step S3 into the Expression 7 (step S4).

Pulse rate (pulses/min)=Maximum Frequency $fMmax$ (Hz)×60         (Expression 7)

Next, the CPU 110 determines whether the start/stop button 106 is pressed so as for the user to stop measuring the pulse rate (step S5). When the determined result is "NO", the CPU 110 returns the routine to step S1 so as to continuously measure the pulse rate. On the other hand, when the determined result is "YES", the CPU 110 stops outputting the control signal to the A/D converting circuit 126 (step S6) and stops the operation of the A/D converting circuit 126.

Figure 15:
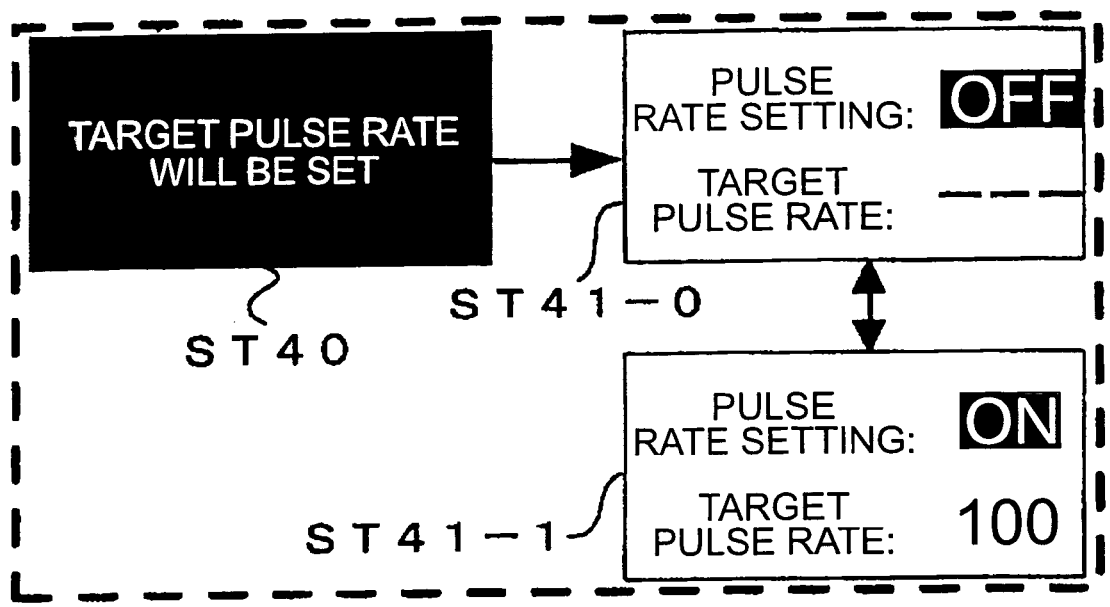
FIG. 15 is a schematic illustrating transition of the display screen.

The detailed operation when the body motion detector 2 is used is explained in detail below. When the body motion detector 2 is initially used, the user set the date and the current time similarly to the body motion detector 1. Then, the user sets walking intensity (i.e., the reference amplitude level), the number of walking pitches (i.e., the reference period), the number of steps (i.e., the reference motion frequency), and ON/OFF of the alarm that are the determination conditions when the CPU 110 operates the alarm generator 1115. According to the body motion detector 2, after the number of steps and the alarm are set in the step number setting screen ST11-1 illustrated in FIG. 12, as illustrated in FIG. 15, a target pulse rate setting and notifying screen ST40 is displayed on the liquid crystal display part 102 so as to urge the user to input the target pulse rate. At this time, when the user presses the button switch 103, the CPU 110 causes a target pulse rate setting screen ST41-0 to be displayed on the liquid crystal display part 102.

In the target pulse rate setting screens ST41-0 and ST41-1, the user sets the target pulse rate to be targeted while taking a walk, and changes walking intensity (i.e., the reference amplitude level) and the number of walking pitches (i.e., the reference period) that are determination conditions of determining whether to operate the alarm generator 115 in accordance with the target pulse rate and the pulse rate while taking a walk. More specifically, when the pulse rate while taking a walk is above the target pulse rate+10, the CPU 110 determines that exercise load is excessively large thereby to reduce walking intensity by one step or to reduce the upper limit value and the lower limit value of the number of walking pitches by 5 (steps/min). To the contrary, when the pulse rate while taking a walk is below the target pulse rate −10, the CPU 110 determines that the exercise load is short thereby to increase walking intensity by one step or to increase the upper limit value and the lower limit value of the number of walking pitches by 5 (steps/min). As a result, the user can take a walk while maintaining the target pulse rate within the range of ±10 when the user takes a walk so as to obtain the alarm sound which is continuously generated. Therefore, the body motion detector 2 can be used to walk in the heart disease rehabilitation in which the management of the pulse rate is important.

It is possible to arbitrarily set the target pulse rate that is a reference for whether to change walking intensity (i.e., the reference amplitude level) and the number of walking pitches (i.e., the reference period) as ±5, ±15 and so on in addition to ±10.

The target pulse rate is set similarly to the order described with respect to walking pitch number setting screens ST9-0 and ST9-1. In the target pulse rate setting screens ST41-0 or ST41-1, when the user presses the button switch 103, the CPU 110 causes the set target pulse rate to be stored in the RAM 112 and causes the setting termination notifying screen ST12 (see FIG. 12) to be displayed on the liquid crystal display part 102 so as to notify the user that the setting is completed. When the user presses the button switch 103, the CPU 110 causes the standard screen ST1 to be displayed on the liquid crystal display part 102 thereby to complete the setting of various information items.

When it is notified whether the user makes appropriate motion using the body motion detector 2 whenever the user takes a walk, the user takes a walk in a state where the standard screen ST1 is displayed on the liquid crystal display part 102 similarly to the body motion detector 1. In this regard, as mentioned above, the CPU 110 determines whether to operate the alarm generator 115 from the acceleration signal of arm shaking, which accompanies walking, outputted from the rectangular wave converting circuit 109, and the values set in walking intensity setting screen, walking pitch number setting screen, and the walk number setting screen, and notifies whether the user makes appropriate motion. Next, as mentioned above, the CPU 110 counts the number of steps, causes the number of steps to be stored in the RAM 112, and updates display of the total number of steps per day on the standard screen ST1.

Figure 14:
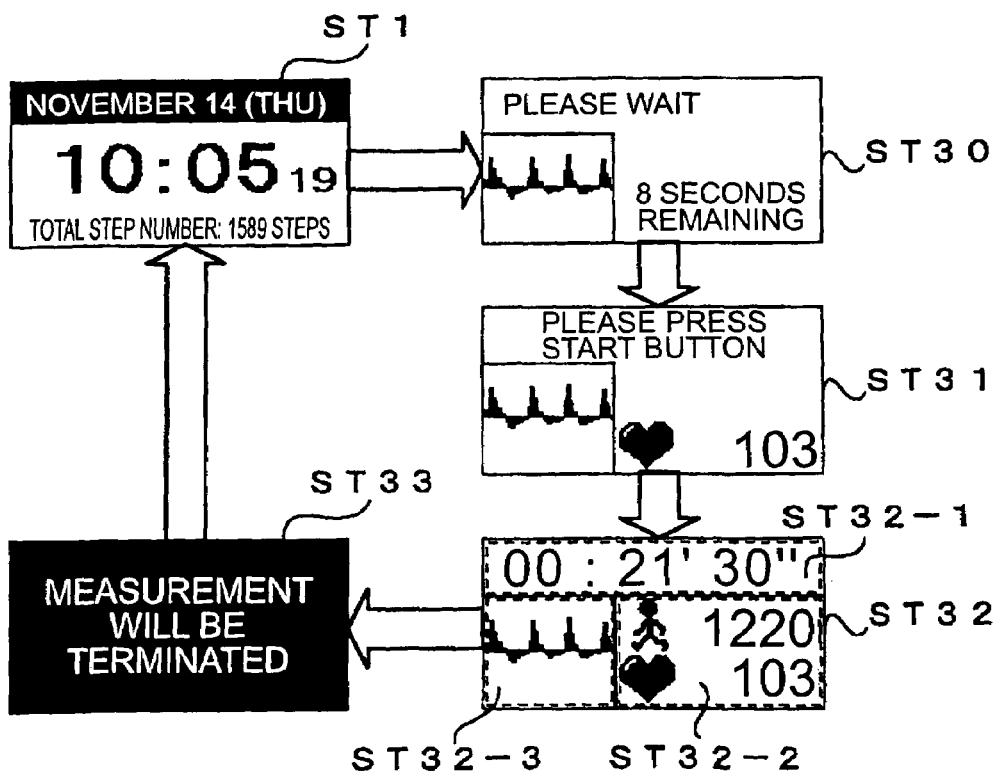
FIG. 14 is a schematic illustrating transition of the display screen.

Furthermore, according to the body motion detector 2, in case that the pulse rate while exercising is measured, the user presses the start/stop button 106 in a state where the standard screen ST1 is displayed on the liquid crystal display part 102. When such manipulation is sensed, the CPU 110 starts the above-mentioned interrupt processing (see FIG. 10) thereby to start measuring the pulse rate. At that time, the CPU 110 causes a pulse measurement-preparing screen ST30 to be displayed on the liquid crystal display part 102, as illustrated in FIG. 14, until the range of the fluctuation in the pulse rate, which is outputted from the frequency analyzing circuit 127, is within a predetermined range.

Then, the CPU 110 causes a measurement start instructing screen ST31 to urge the user to instruct the measurement of the pulse rate to be displayed on the liquid crystal display part 102 after the range of the fluctuation of the pulse rate falls within a predetermined range. When the user presses the start/stop button 106 so as to start measuring the pulse rate, the CPU 110 senses the related manipulation thereby to perform the above-mentioned interrupt processing and causes a measurement screen ST32 showing the measured pulse rate and the number of steps while exercising to be displayed.

More specifically, the measuring screen ST32 includes a lapsed time display region ST32-1 to display the lapsed time from the start of motion, a measured value display region ST32-2 to display the measured value of the pulse rate and the number of steps while exercising, and a pulse wave display region ST32-3 to display a pulse waveform. The number of steps while exercising is displayed on the right side of a mark showing that a person is walking, at the upper end of the measured value display region ST32-2. The pulse rate is displayed together with a heart mark at the lower end thereof.

Next, the user presses the start/stop button 106 so as to stop measuring pulses after stopping walking. When CPU 100 detects such manipulation, it stops the output to the A/D converting circuit 126 is stopped thereby to stop outputting the pulse wave signal and the acceleration signal from the A/D converting circuit 126 to the frequency analyzing circuit 127. Then, the CPU 110 causes the measurement result to be stored in the RAM 112 and causes a measurement termination notifying screen ST33 to be displayed on the liquid crystal display part 102. In the measurement termination notifying screen ST33, When the user presses the start/stop button 106 once more, the standard display screen ST1 is displayed. At this time, the total number of steps obtained by adding the number of steps while exercising to the total number of steps before making motion is displayed on the standard display screen ST1.

In the body motion detector 2, in case that various information items such the total walking time, the total number of walks, and the total exercise amount per day, which are stored in the RAM 112 are caused to be displayed on the liquid crystal display part 102, the user presses the button switch 104 similarly to the order (see FIG. 13) described with respect to the body motion detector 1 in a state where the standard screen ST1 is displayed.

Figure 16:
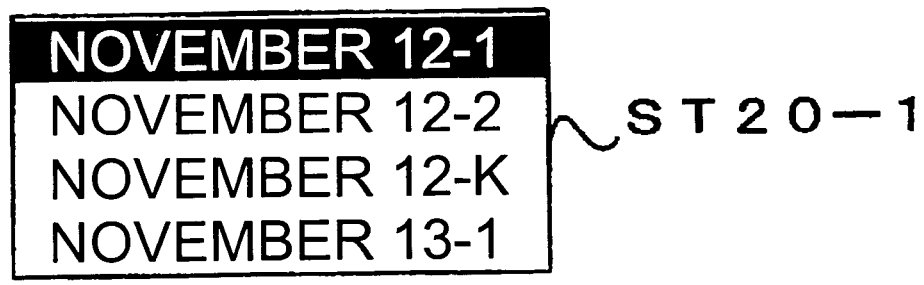
FIG. 16 is a schematic illustrating the display screen.

When such manipulation is sensed, as illustrated in FIG. 16, the CPU 110 causes a date selecting screen ST20-1 to urge the user to select the date to be displayed to display a measurement result, to be displayed on the liquid crystal display part. In the date selecting screen ST20-1, the display of the selected date is reversed. Therefore, in order select the date, the user presses the start/stop button 106. In FIG. 16, "November 12-1" and "November 12-2" displayed on the date selecting screen ST20-1 indicate the first and second exercise results of November 12. "November 12-K" indicates the sum of the motion frequency of November 12.

Hereinafter, the result display notifying screen ST21, the daily exercise amount displaying screen ST22, and the result display termination notifying screen ST23 are displayed similarly to the order (see FIG. 13) descried with respect to the body motion detector 1 and then the standard screen ST1 is displayed again.

As mentioned above, according to the body motion detector 1 and the body motion detector 2 according to the present exemplary embodiment, the user previously sets the motion intensity (the reference amplitude level), the number of walking pitches (the reference period), and the number of walks (the reference motion frequency) that enables the user to make appropriate motion thereby to check whether he/she makes appropriate motion whenever taking a walk and to maintain the appropriate motion. Therefore the user can obtain an excellent exercise effect when he/she takes a walk so as to obtain an alarm continuously. Furthermore, as mentioned above, the body motion detector 1 and the body motion detector 2 count the frequency, by which the user takes a walk with appropriate motion, and display the value on the liquid crystal display part 102. Therefore, the body motion detector 1 and the body motion detector 2 can also be used as a pedometer (a registered trademark).

In the body motion detector 2, when a difference between the target pulse rate and the pulse rate while taking a walk is larger than a predetermined value, it is possible to change walking intensity (the reference amplitude level) or the number of walking pitches (the reference period) that is the determination condition of determining whether to operate the alarm generator 115. Therefore, when the user can take a walk within a range of the target pulse rate ±10 by taking a walk, he/she maintains a walk so as to obtain the alarm sound to notify that the user exercises within a normal range which sound is continuously generated. Therefore, the body motion detector 2 can be used to walk in the heart disease rehabilitation in which the management of the pulse rate is important.

EXEMPLARY MODIFICATIONS

The above-mentioned exemplary embodiments illustrate one aspect of the present invention and can be arbitrarily modified within the scope of the present invention. Various exemplary modifications are described below.

Exemplary Modification 1

According to the above-mentioned exemplary embodiments, walking is detected as body motion of a user and it is notified that the user appropriately exercises when the user makes appropriate motion. However, the present invention is not limited thereto. For example, when the user makes repetitive motion such as a chin-up exercise, an exercise to strengthen the abdominal muscle, and a rope skipping exercise, it is possible to determine whether the user makes appropriate motion by the amplitude, the period, and the frequency of a body motion signal and to determine whether the user makes appropriate motion thereby to notify the user.

For example, according to the above-mentioned exemplary embodiments, the acceleration sensor unit 107 is provided so as to detect the body motion of the user. However, the present invention is not limited thereto, and it may be configured to detect the body motion of the user, such as walking and running, by including an acceleration sensor or a pressure sensor in the soles of the shoes of the user. Further, it may be configured to detect a change in speed, which accompanies the body motion of the user, by a speed sensor, and to detect a change in an altitude, which accompanies the body motion of the user, by an altimeter.

Exemplary Modification 2

According to the above exemplary embodiments, the arm-wearing-type body motion detector mounted around a user's arm, has been illustrated. However, the present invention is not limited thereto. For example, in the body motion detector 1 illustrated in FIG. 1, the user may wear the wristband 101 on a user's leg or head by forming the wristband 101 of an elastic material such as rubber. Further, the body motion detector may be loaded in a user's belt like a common waist-wearing pedometer (a registered trademark) provided with a clip in the back side of the main body 100.

Therefore, the body motion detector can be used for a cycling exercise accompanied by bending and stretching the legs of the user, the exercise to strengthen the abdominal and spinal muscles which is accompanied by vertically shaking the head of the user, and a squat exercise accompanied by vertically shaking the waist of the user without being limited to the motion that accompanies arn-shaking such as walking and running.

Exemplary Modification 3

Figure 5:
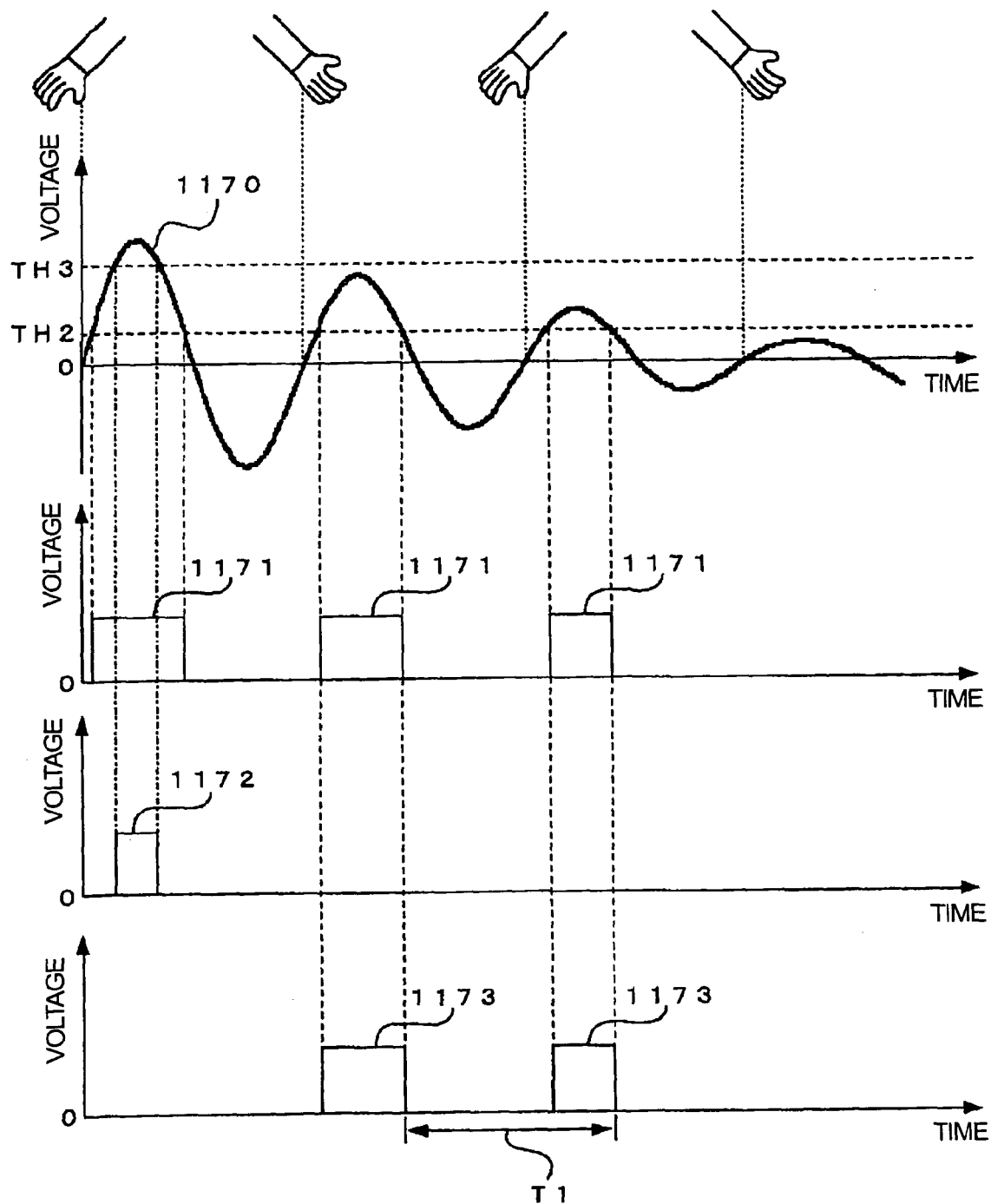
FIG. 5 is a schematic showing the operation of the rectangular wave circuit.

According to the above-mentioned exemplary embodiments, when the rectangular wave converting circuit 109 forms rectangular wave pulses that are walking detecting signals, as illustrated in FIG. 4, the rectangular wave pulses 161 that are walking detecting signals are formed using the threshold TH1. However, the present invention is not limited thereto. As illustrated in FIG. 5, the range of the amplitude value of the acceleration from a threshold TH2 to a threshold TH3 may be set. In this case, when the amplitude value of an acceleration signal 1170 from the acceleration signal amplifying circuit 108 exceeds the threshold TH2 and the threshold TH3, the rectangular wave converting circuit 109 forms rectangular wave pulses 1171 and rectangular wave pulses 1172. In this regard, the CPU 110 determines that the rectangular wave pulses 1171 are walking detecting signals if the rectangular wave pulses 1172 are not detected while the rectangular wave pulses 1171 is detected. That is, rectangular wave pulses 1173 are walking-detecting signals. The rectangular wave converting circuit 109 outputs walking-detecting signals to the CPU 110 whenever the rectangular wave pulses 1173 are formed. Then, the CPU 110 operates the alarm generator 115 whenever walking detecting signals are received from the rectangular wave converting circuit 109 thereby to notify the user that he/she is making a predetermined motion.

Therefore, it is possible to prevent the user from taking such a weak arm-shaking walking that the amplitude value of the acceleration of arm-shaking in walking is less than the threshold TH2 and from taking such a strong arm-shaking walking that the amplitude value exceeds the threshold TH3, and thereby to notify a more appropriate motion to the user.

Exemplary Modification 4

According to the above-mentioned exemplary embodiments, the CPU 110 calculates the reference period that is a determination condition of determining walking-detecting signal from the number of walking pitches input by the user. However, the present invention is not limited thereto. The user may input the number of steps and walking time (min) that are aimed by the user to the input part 114 and the reference period may be calculated from the input value.

Here, the CPU 110, as illustrated in the Expression 9, obtains the number of steps per unit time, that is, the number of walking pitches (steps/min) from the input number of steps (step) and walking time (min), calculates the reference period by substituting the number of walking pitches into the Expression 4, and causes the reference period to be stored in the RAM 112.

Number of Walking pitches (steps/min)=Number of steps (step)/Walking time (min)    (Expression 9)

Furthermore, the reference period that is a determination condition when the CPU 110 determines walking detecting signal may be calculated by inputting the exercise amount (kcal) and walking time (min) that are aimed by the user and the personal information of the user such as the height and the weight to the input part 114.

As a method of calculating the reference period, the modification of the Expression 2 derives the Expression 10. The METS is obtained by substituting the inputted exercise amount, weight, and walking time into the Expression 10.

METS≈Exercise amount (kcal)/Weight (kg)/Walking time (hour)    (Expression 10)

Walking speed is specified from the Expression 9, which is converted to simply and easily calculate the METS and the correspondence relationship between the METS and walking speed. As illustrated in the Expression 10, walking speed is walking distance per unit walking time. Walking distance is calculated by multiplying the step by the number of steps.

Therefore, as derived from the Expression 7, the number of steps per unit time, that is, the number of walking pitches (steps/min) is obtained by dividing walking speed by the number of steps. The reference period is calculated by substituting the number of walking pitches into the Expression 4. The CPU 110 calculates the reference period as mentioned above and causes the obtained reference period to be stored in the RAM 112.

Exemplary Modification 5

According to the above-mentioned exemplary embodiments, the pulse rate of the user is obtained by the pulse wave sensor unit 121 of the body motion detector 2. However, the present invention is not limited thereto. It is possible to detect a change in the pressure caused by the contraction of vessels by a pressure sensor and then to obtain the pulse rate from the change in the pressure. Furthermore, it is possible to detect a change in blood flow rate, which accompanies the pulses, by an ultrasonic sensor and to obtain the pulse rate from a blood flow rate change signal.

Exemplary Modification 6

According to the above-mentioned exemplary embodiments, the pulse rate of the user is obtained by the pulse wave sensor unit 121 of the body motion detector 2 and, when the pulse rate is beyond the range of the target pulse rate set by the user, the reference range of the motion is changed so as to be within the range of the target pulse rate. However, the present invention is not limited thereto. It is possible to obtain the biological reaction information accompanying the motion, such as blood pressure by the pressure sensor, an oxygen concentration in blood by an optical sensor, and perspiration by a perspiration sensor and to change the reference range of the motion from such measured values and the target values set by the user.

[Advantages]

As mentioned above, according to the present invention, while making repetitive motion such as walking and running, it is possible to provide a body motion detector capable of notifying appropriate motion to the user for every motion. Therefore, the user can make motion while checking that he/she makes appropriate motion and while maintaining the motion in an appropriate range.

What is claimed is:

1. A body motion detector for use with a user, comprising:
   a body motion detecting device to detect body motion accompanying repetitive motion of the user;
   a determining device to determine whether an amplitude value of a detection result of the body motion detecting device is within a predetermined reference range, the detection result being either the motion intensity and accumulated motion frequency of the repetitive motion or the motion intensity, motion period, and accumulated motion frequency of the repetitive motion, and the predetermined reference range for the motion intensity and the motion period being either above the lower limit reference value set by the user or between the lower limit reference value and the upper limit reference value, which are set by the user, and the predetermined reference range for the accumulated motion frequency being below an accumulated target frequency set by the user;
   a rectangular wave converting circuit that converts the detection result only when the amplitude value is within the predetermined reference range; and
   a notifying device to generate a notifying signal whenever a determination result by the determining device is within the predetermined reference range.

2. The body motion detector according to claim 1, the reference range for the motion period being calculated from motion time and an accumulated motion frequency, which are set as targets by the user.

3. The body motion detector according to claim 1, the reference range for the motion period being calculated from motion time and motion calories consumed, which are set as targets by the user.

4. The body motion detector according to claim 1, when the accumulated motion frequency reaches the accumulated target frequency, the notifying device generating a notifying signal different from the notifying signal and resets the accumulated motion frequency to 0.

5. The body motion detector according to claim 1, the body motion detecting device including at least one of an acceleration sensor, a pressure sensor, and a speed sensor.

6. The body motion detector according to claim 1, the notifying signal being at least one of sound from an alarm, vibration from a vibration motor, and light from an LED (light emitting diode).

7. The body motion detector according to claim 1, the body motion detector being an arm-wearing type device.

8. A body motion detector for use with a user, comprising:
   a body motion detecting device to detect body motion accompanying repetitive motion of the user;
   a determining device to determine whether an amplitude of a detection result of the body motion detecting device is within a predetermined reference range, the detection result being either the motion intensity and accumulated motion frequency of the repetitive motion or the motion intensity, motion period, and accumulated motion frequency of the repetitive motion; and the predetermined reference range for the motion intensity and the motion period being either above the lower limit reference value set by the user or between the lower limit reference value and the upper limit reference value, which are set by the user, and the predetermined reference range for the accumulated motion frequency being below an accumulated target frequency set by the user;
   a rectangular wave converting circuit that converts the detection result only when the amplitude value is within the predetermined reference range;
   a notifying device to generate a notifying signal whenever a determination result by the determining device is within the predetermined reference range;

a biological reaction detecting device to detect a biological reaction of the user; and a calculating device to calculate a reference range from the detection result of the biological reaction detecting device.

9. The body motion detector according to claim 8, the biological reaction detecting device including a pulse wave detecting device to detect a pulse wave of the user; and a pulse rate calculating device to calculate a pulse rate of the user from the detection result of the body motion detecting device and the detection result of the pulse wave detecting device.

10. The body motion detector according to claim 9, the predetermined reference range being changed when the pulse rate is beyond the range of a target pulse rate previously set by the user, so that the calculated pulse rate is within the range of the target pulse rate, even if the determination result is within the predetermined reference range.

11. The body motion detector according to claim 9, the pulse rate calculating device analyzing frequencies of the detection signals of the pulse wave detecting device and the body motion detecting device using FFT (fast Fourier transform) processing.

12. The body motion detector according to claim 8, the body motion detector being an arm-wearing type device.

13. A body motion detector for use with a user, comprising:

a body motion detecting device to detect body motion accompanying repetitive motion of the user;

a determining device to determine whether a detection result of the body motion detecting device is within a predetermined reference range;

a notifying device to generate a notifying signal whenever a determination result by the determining device is within the predetermined reference range;

a biological reaction detecting device to detect a biological reaction of the user; and a calculating device to calculate a reference range from the detection result of the biological reaction detecting device, the biological reaction detecting device including:

a pulse wave detecting device to detect a pulse wave of the user, and a pulse rate calculating device to calculate a pulse rate of the user from the detection result of the body motion detecting device and the detection result of the pulse wave detecting device; and a rectangular wave converting circuit that converts the detection result only when an amplitude value is within the predetermined reference range.

* * * * *